(12) United States Patent
Wang et al.

(10) Patent No.: US 11,197,610 B2
(45) Date of Patent: Dec. 14, 2021

(54) SMART TERMINAL AND SMART WRISTWATCH

(71) Applicant: GOERTEK INC., Shandong (CN)

(72) Inventors: Lin Wang, Weifang (CN); Peijie Zhao, Weifang (CN); Jianguo Zhang, Weifang (CN); Chao Yi, Weifang (CN)

(73) Assignee: GOERTEK INC., Weifang (CN)

( * ) Notice: Subject to any disclaimer, the term of this patent is extended or adjusted under 35 U.S.C. 154(b) by 350 days.

(21) Appl. No.: 15/753,957

(22) PCT Filed: Jul. 8, 2016

(86) PCT No.: PCT/CN2016/089375
§ 371 (c)(1),
(2) Date: Feb. 21, 2018

(87) PCT Pub. No.: WO2017/032175
PCT Pub. Date: Mar. 2, 2017

(65) Prior Publication Data
US 2018/0228370 A1 Aug. 16, 2018

(30) Foreign Application Priority Data
Aug. 21, 2015 (CN) .......................... 201520636898.1

(51) Int. Cl.
*A61B 5/021* (2006.01)
*A61B 5/00* (2006.01)
(Continued)

(52) U.S. Cl.
CPC .......... *A61B 5/0022* (2013.01); *A61B 5/0205* (2013.01); *A61B 5/02055* (2013.01);
(Continued)

(58) Field of Classification Search
CPC ....... A61B 5/00; A61B 5/0205; A61B 5/0022; A61B 5/02055; A61B 5/681; A61B 5/024; A61B 5/021; G04D 99/00; H04W 88/02
See application file for complete search history.

(56) References Cited

U.S. PATENT DOCUMENTS

2015/0091764 A1\* 4/2015 Hsieh ....................... H01Q 7/00
343/702
2016/0062417 A1\* 3/2016 Chu ...................... G06F 1/1698
600/390
(Continued)

FOREIGN PATENT DOCUMENTS

CN 203107107 U 8/2013
CN 103271725 A 9/2013
(Continued)

*Primary Examiner* — Eric J Messersmith
(74) *Attorney, Agent, or Firm* — Maschoff Brennan

(57) ABSTRACT

The present invention discloses a smart terminal and a smart wrist watch. The smart terminal comprises a metal housing, a wireless communication unit, a human body information detection unit and a signal selection unit, wherein the wireless communication unit comprises a wireless antenna, all or part of the metal housing is used as an antenna area for setting the wireless antenna, a common conductor is provided for the antenna area; the human body information detection unit comprises at least two detection contact points, one of the detection contact points is provided in the antenna area; the detection contact point in the antenna area and the wireless antenna are connected with one end of the common conductor, respectively, the other end of the common conductor is connected with the signal selection unit; the signal selection unit screens out a signal from the wireless antenna out of a signal transmitted on the common conductor, sends the signal to the wireless communication unit, screens out the signal from the detection contact point
(Continued)

and sends the signal to the human body information detection unit. The present invention provides a solution solving the problem that the test result of the smart terminal in the prior art is not accurate enough due to the size limitation.

6 Claims, 4 Drawing Sheets

(51) Int. Cl.
    *A61B 5/0205*     (2006.01)
    *G04D 99/00*     (2006.01)
    *A61B 5/024*     (2006.01)
    *H04W 88/02*     (2009.01)

(52) U.S. Cl.
    CPC .............. *A61B 5/681* (2013.01); *G04D 99/00* (2013.01); *A61B 5/021* (2013.01); *A61B 5/024* (2013.01); *H04W 88/02* (2013.01)

(56) References Cited

U.S. PATENT DOCUMENTS

2016/0360986 A1\* 12/2016 Lange ................... A61B 5/7275
2017/0000415 A1\* 1/2017 Lapetina ............... A61B 5/6843

FOREIGN PATENT DOCUMENTS

| CN | 203914894 U | 11/2014 |
| CN | 204009393 U | 12/2014 |
| CN | 204971247 U | 1/2016 |

\* cited by examiner

SMART TERMINAL AND SMART WRISTWATCH

CROSS-REFERENCE TO RELATED APPLICATIONS

This application is the U.S. national stage of International Application No. PCT/CN2016/089375, filed Jul. 8, 2016, which claims priority to Chinese Patent Application No. 201520636898.1, filed Aug. 21, 2015, both of which are incorporated herein by reference.

TECHNICAL FIELD OF THE INVENTION

The present invention relates to the field of manufacturing technology of a wearable device, and more particularly to a smart terminal and a smart wrist watch.

BACKGROUND OF THE INVENTION

With the development of smart equipment, the functions of wearable equipment also become more and more. Furthermore, because people concern their own health, the detection functions in human health aspects may be increased in a smart wrist watch.

A wearable smart wrist watch in the prior art increases a heart rate detection function, and whether a heart rate is got via measuring the resistance between two points through a bio-electrical impedance analysis, that is through the introduction of one micro-current in a human body, or electrocardiography is obtained to get a real-time heart rate through a bio-potential sensing technology, that is through the manner that a potential change is led from a body surface, it is needed to have two contact points and a good contact between a test point and human skin during the measurement.

For the wearable equipment of the wrist watch in the prior art, these two contact points are generally provided in the back of the wrist watch to reach the purpose of the contact with the wrist skin. However, for a wearable product in the prior art, limited by the size of the wrist watch, the distance between the two points are generally close, and the contact area is relatively small, affecting the stability of a test result.

SUMMARY OF THE PRESENT INVENTION

The present invention provides a smart terminal and a smart wrist watch. The smart terminal provided by the present invention may solve the problem that the smart terminal in the prior art has the limited size, the closer distance between the two detection points and the smaller contact area, which lead to the inaccurate test result.

The present invention discloses a smart terminal, including a metal housing, a wireless communication unit, a human body information detection unit and a signal selection unit for screening out a signal, the wireless communication unit includes a wireless antenna, all or part of the metal housing is used as an antenna area for setting the wireless antenna, a common conductor is provided for the antenna area;

the human body information detection unit includes at least two detection contact points, one of the detection contact points is provided in the antenna area;

the detection contact point in the antenna area and the wireless antenna are connected with one end of the common conductor, respectively, the other end of the common conductor is connected with the signal selection unit;

the signal selection unit screens out the signal from the wireless antenna out of the signal transmitted on the common conductor, sends the signal to the wireless communication unit, screens out a signal from the detection contact point out of the signal transmitted on the common conductor and sends the signal to the human body information detection unit.

The present invention still discloses a smart wrist watch, including a metal watch casing, a wireless communication unit provided in the watch casing, a human body information detection unit, and a signal selection unit for screening out a signal;

the wireless communication unit includes a wireless antenna, all or part of the metal watch casing is used as an antenna area for setting the wireless antenna, a common conductor is provided for the antenna area;

the human body information detection unit includes at least two detection contact points, one of the detection contact points is provided in the antenna area;

the detection contact point in the antenna area and the wireless antenna are connected with one end of the common conductor, respectively, the other end of the common conductor is connected with the signal selection unit;

the signal selection unit screens out a signal from the wireless antenna out of a signal transmitted on the common conductor, sends the signal to the wireless communication unit, screens out a signal from the detection contact point out of the signal transmitted on the common conductor and sends the signal to the human body information detection unit.

The present invention still discloses a smart wrist watch, including a metal watch band, a wireless communication unit of which at least part of a wireless antenna is provided on the metal watch band, a human body information detection unit provided in a watch casing, and a signal selection unit for screening out a signal;

the wireless communication unit includes a wireless antenna, all or part of the metal watch band is used as an antenna area for setting the wireless antenna, a common conductor is provided for the antenna area;

the human body information detection unit includes at least two detection contact points, one of the detection contact points is provided in the antenna area;

the detection contact point in the antenna area and the wireless antenna are connected with one end of the common conductor, respectively, the other end of the common conductor is connected with the signal selection unit;

the signal selection unit screens out a signal from the wireless antenna out of a signal transmitted on the common conductor, sends the signal to the wireless communication unit, screens out a signal from the detection contact point out of the signal transmitted on the common conductor and sends the signal to the human body information detection unit.

As described above, according to the technical solution provided by the present invention, all or a part of the metal housing is provided as the antenna area and the detection point of the human body information detection unit is provided in the antenna area so that the distance of the two contact points of the human body information detection unit is short, and the contact area between the detection point and the human body may be increased, thus improving the stability of the test results of the human body information detection unit. Furthermore, in the present invention, the detection contact point of the human body information detection unit shares the conductor with the wireless antenna, saving the separately provided detection contact point and the corresponding alignment, so that the overall structure of the smart terminal is more compact, and the human body information data collected by the human body information detection unit is more accurate.

EMBODIMENTS OF THE PRESENT INVENTION

The objects, technical solution and advantages of the present invention will become more apparent from the following further detailed description of embodiments of the present invention in conjunction with the accompanying drawings.

Figure 1:
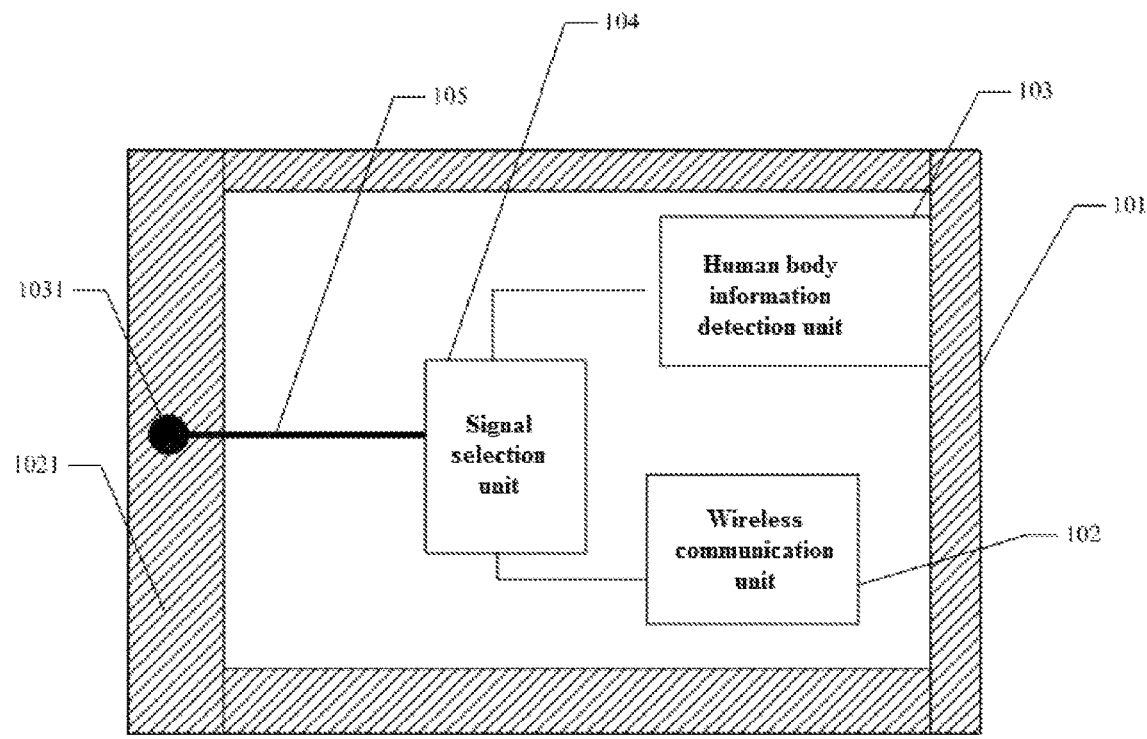
FIG. 1 is a structural diagram of a smart terminal in the present invention.

FIG. 1 is a structural diagram of a smart terminal in the present invention. As shown in FIG. 1, the smart terminal includes a metal housing 101, a wireless communication unit 102, a human body information detection unit 103 and a signal selection unit 104 for screening out a signal, The wireless communication unit 102 includes the wireless antenna 1021, all or part of the metal housing 101 is used as an antenna area for setting the wireless antenna 1021, and a common conductor 105 is provided for the antenna area; in the embodiment, as shown in FIG. 1, the hatched portion in the figure is the antenna area in which the wireless antenna 1021 is provided, that is, the entirety of the entire metal housing 101 is taken as the wireless antenna 1021. The wireless antenna 1021 is used for transmitting and receiving a wireless signal.

In order to reduce the volume occupied by the wireless antenna in the smart terminal, and make the outline and shape of the smart terminal more compact, all of the metal housing 101 may be used as the wireless antenna 1021; as shown in FIG. 1, in other embodiments of the present invention, only a portion of the metal housing 101 may be used as the wireless antenna 1021. For example, the partial metal housing 101 shown in the leftmost hatched portion of FIG. 1 may be used as the wireless antenna 1021.

In the specific implementation way, the entire metal housing 101 may be provided as the wireless antenna 1021 or a portion of the metal housing 101 may be provided as the wireless antenna 1021 by selecting the structure of the smart terminal and the specifications of the desired antenna. Repeatability will not be carried out here.

As shown in FIG. 1, the human body information detection unit 103 is further provided in the smart terminal of the present invention. The human body information detection unit 103 is used for detecting the human body information data; in order to be able to better detect the human body information data, the body information detection unit 103 includes at least two detection contact points 1031, one of the detection contact points 1031 is provided in the antenna area; the detection contact point 1031 and the wireless antenna 1021 in the antenna area are connected with one end of the common conductor 105, respectively, and the other end of the common conductor 105 is connected with the signal selection unit 104; that is, in the present invention, since the detection contact 1031 and the wireless antenna 1021 of the human body information detection unit 103 provided in the antenna area are both connected with the common conductor 105, the data of the human body information collected by one detection contact point 1031 in the human body information detection unit 103 and a signal collected by the wireless antenna 1021 are both transmitted to the signal selection unit 104 through the common conductor 105.

In the above-described embodiments of the present invention, the signal selection unit 104 screens out a signal from the wireless antenna 1021 out of signals transmitted on the common conductor 105, sends the signal to the wireless communication unit, screens out a signal from the detection contact point 1031 out of the signals transmitted on the common conductor 105 and sends the signal to the human body information detection unit 103. That is, the signal selection unit 104 is capable of receiving the signals transmitted from the common conductor 105, and screening out the wireless signals from the wireless antenna 1021 and the signals of the human body information from the detection contact point 1031 of the human body information detection unit 103, respectively.

In one embodiment of the present invention, human body information data detected by the detection contact point 1031 include one or more of heart rate data, blood pressure data, pulse data and body temperature data; the human body information detection unit 103 calculates the human body state detection result based on the human body information data detected by the detection contact point 1031.

In one embodiment of the present invention, the body information detection unit 103 may be a heart rate detection module, and the heart rate detection module is provided with two detection contact points. One detection contact point is provided on the back of the smart terminal and in contact with the human skin; and the other detection contact point is provided in the antenna area. The heart rate data of the human body is detected by detecting the contact point, and the detected heart rate data are sent to the heart rate detection module, and the heart rate detection module calculates the psychological result of the human body based on the detected heart rate data.

Figure 2:
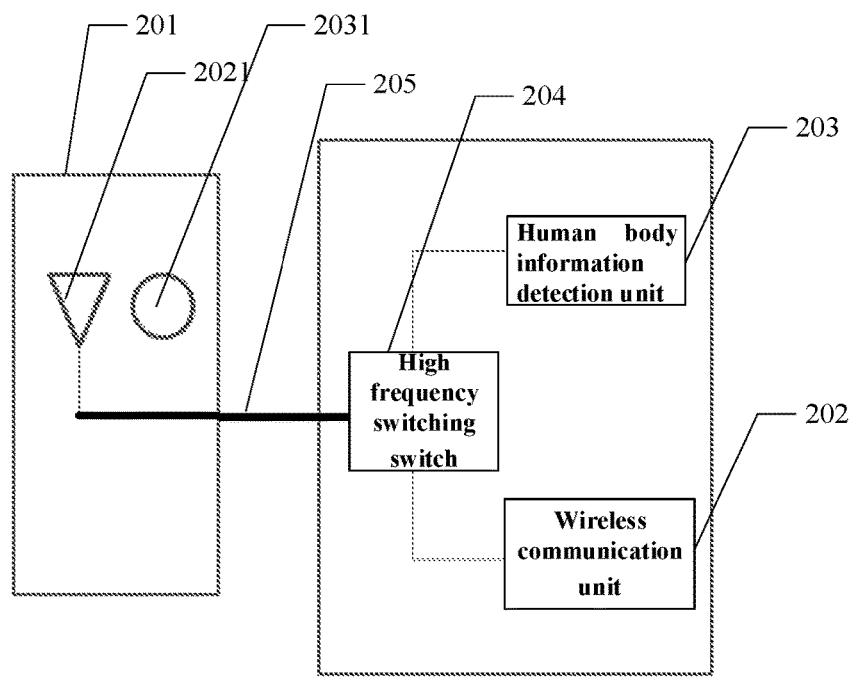
FIG. 2 is a detailed structural diagram of a smart terminal in Embodiment 1 of the present invention.

FIG. 2 is a detailed structural diagram of a smart terminal in Embodiment 1 of the present invention. As shown in FIG. 2, in the embodiment, the signal selection unit includes a high frequency switch 204; the wireless antenna 2021 and the detection contact point 2031 are provided in the corresponding antenna area 201.

The high frequency switch 204 screens out a signal having a frequency higher than a first preset value from the signal transmitted on the common conductor 205, to use the signal as the signal from the wireless antenna 2021, and the high frequency switch gets through a branch connected with the wireless communication unit 202, and shuts down a branch connected with the human body information detection unit 203, to send the signal which is screened out to the wireless communication unit 202;

the high frequency switch screens out a signal having a frequency higher than a second preset value from the signal transmitted on the common conductor, to use the signal as the signal from the wireless antenna 2031, and the high frequency switch shuts down a branch connected with the wireless communication unit 202, and gets through the branch connected with the human body information detection unit 203, to send the signal which is screened out to the human body information detection unit 203.

In one embodiment of the present invention, the frequency of the wireless signal received by the wireless antenna 2021 belongs to a high frequency signal, which is basically more than 2.4 GHz, the frequency of the signal received by the detection contact point 2031 belongs to a low frequency signal, which is substantially within 200 Hz, and therefore, by setting the high frequency switch 204, only the branch connected with the wireless communication unit 202 is connected when the high frequency signal is received; and only the branch connected with the human body information detection unit 203 is connected when the low frequency signal is received, thus achieving the screening out of the signals collected respectively.

Figure 3:
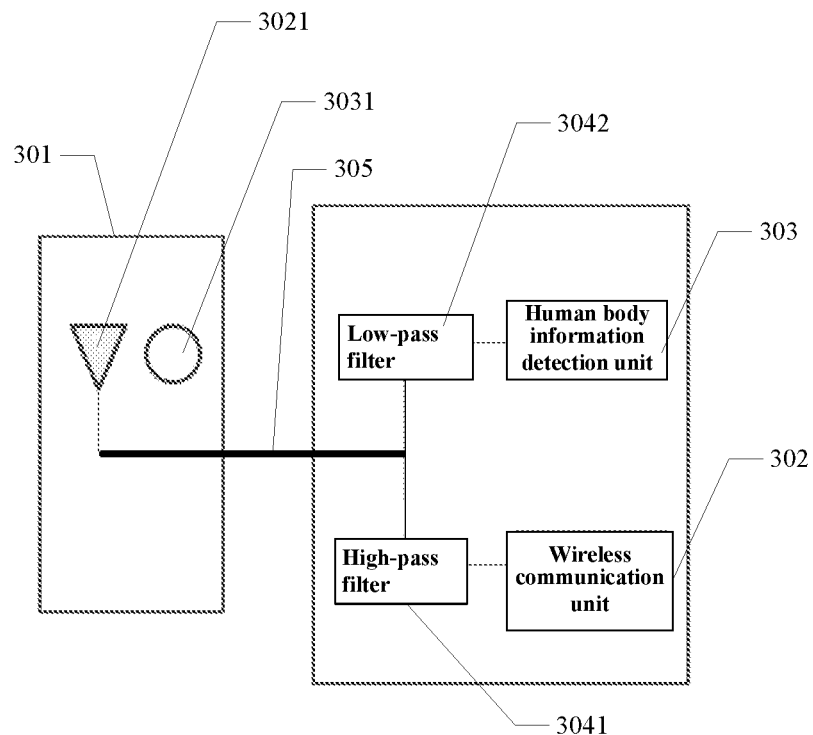
FIG. 3 is a detailed structural diagram of a smart terminal in Embodiment 2 of the present invention.

FIG. 3 is a detailed structural diagram of a smart terminal in Embodiment 2 of the present invention. As shown in FIG. 3, in the embodiment, the signal selection unit includes a high-pass filter 3041 and a low-pass filter 3042; the wireless antenna 3021 and the detection contact point 3031 are provided in the corresponding antenna area 301.

As shown in FIG. 3, the other end of the common conductor 305 is connected with the high-pass filter 3041 and the low-pass filter 3042, respectively, the high-pass filter 3041 is connected with the wireless communication unit 302, and the low-pass filter 3042 is connected with the human body information detection unit 303.

The high-pass filter 3041 screens out the signal from the wireless antenna 3021 out of the signal transmitted on the common conductor 305 and sends the signal to the wireless communication unit 302, and the low-pass filter 3042 screens out the signal from the detection contact point out of the signal transmitted on the common conductor 305 and sends the signal to the human body information detection unit 303.

In one embodiment of the present invention, the frequency of the wireless signal received by the wireless antenna 3021 belongs to the high frequency signal, which is basically more than 2.4 GHz, the frequency of the signal received by the detection contact point 3031 belongs to the low frequency signal, which is substantially within 200 Hz, furthermore, a low-frequency cutoff frequency of the high-pass filter 3041 may be 2.35 GHz, and therefore, it is possible to efficiently isolate the low-frequency signal from the wireless communication unit 302 by setting the high-frequency filter 3041, that is, only the signal from the wireless antenna 3021 is screened out. A high frequency cutoff frequency of the low pass filter 3042 may be selected to be 300 Hz, so that the wireless signal may be effectively isolated by setting the low pass filter 3042, that is, only the signal from the detection contact 3031 is screened out from the signal transmitted on the common conductor 305, thus achieving the screening out of the signals collected respectively.

Figure 4:
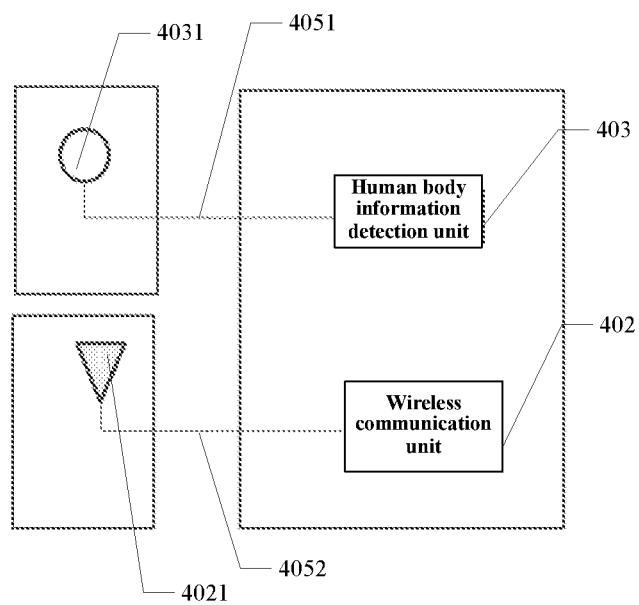
FIG. 4 is a structural diagram of a smart terminal in the prior art.

FIG. 4 is a structural diagram of a smart terminal in the prior art. As shown in FIG. 4, in the smart terminal in the prior art, the wireless communication unit 402 and the wireless antenna 4021 are connected by a first conductor 4052; the human body information detection unit 403 and the detection contact 4031 are connected by a second conductor 4051.

It can be seen that in the smart terminal in the prior art, a separate conductor 4051 for the additional human body information detection unit 403 is needed to be provided. As the smart terminal such as the wrist watch has the defect of a small volume, not only the metal housing additionally provided at the smart terminal in the prior art and the separate conductor compress the overall internal space of the wrist watch, but also the small volume of the metal housing causes the contact area between the human body information detection unit and the human body to be small, and causes the distance between the two detection contact points of the human body information detection unit to be too short, resulting in a problem that the detection result is not accurate enough.

In combination with FIG. 2 and FIG. 3, in the present invention, by setting the wireless antenna and the detection contact point in the antenna area of the metal housing, it is possible to avoid the additional setting of the detection contact point and the compression of the conductor to the internal space of the smart terminal, and it is also possible to reduce the complexity of setting the two conductors on a PCB board circuit inside the smart terminal. In addition, by setting the detection contact point on the metal housing, the contact area between the detection contact point and the human body may be increased while the distance between the detection contact points may be prolonged, thereby improving the accuracy of detection by the human body information detection unit.

In one embodiment of the present invention, the wireless communication unit 302 may be one or more of the followings:

a Bluetooth module, a WIFI module, a radio frequency module, a 3G communication module and a 4G communication module.

In a specific implementation way, the detected human body information data may be displayed directly on the smart terminal; it is also possible to provide a wireless communication module within the smart terminal. The human body information detection unit is connected with the wireless communication module, and transmits, through the wireless communication module, the detected human information data to other external smart devices such as a mobile phone, a tablet computer and so on to be displayed, so that a user may obtain the corresponding human information data conveniently in time.

In the above-described embodiments of the present invention, the signal selection unit 104, the human body information detection unit 103, and the wireless communication unit 102 may be provided on a printed circuit board.

In the above-described embodiment of the present invention, the smart terminal is a wrist watch, a bracelet or a mobile phone.

Figure 5:
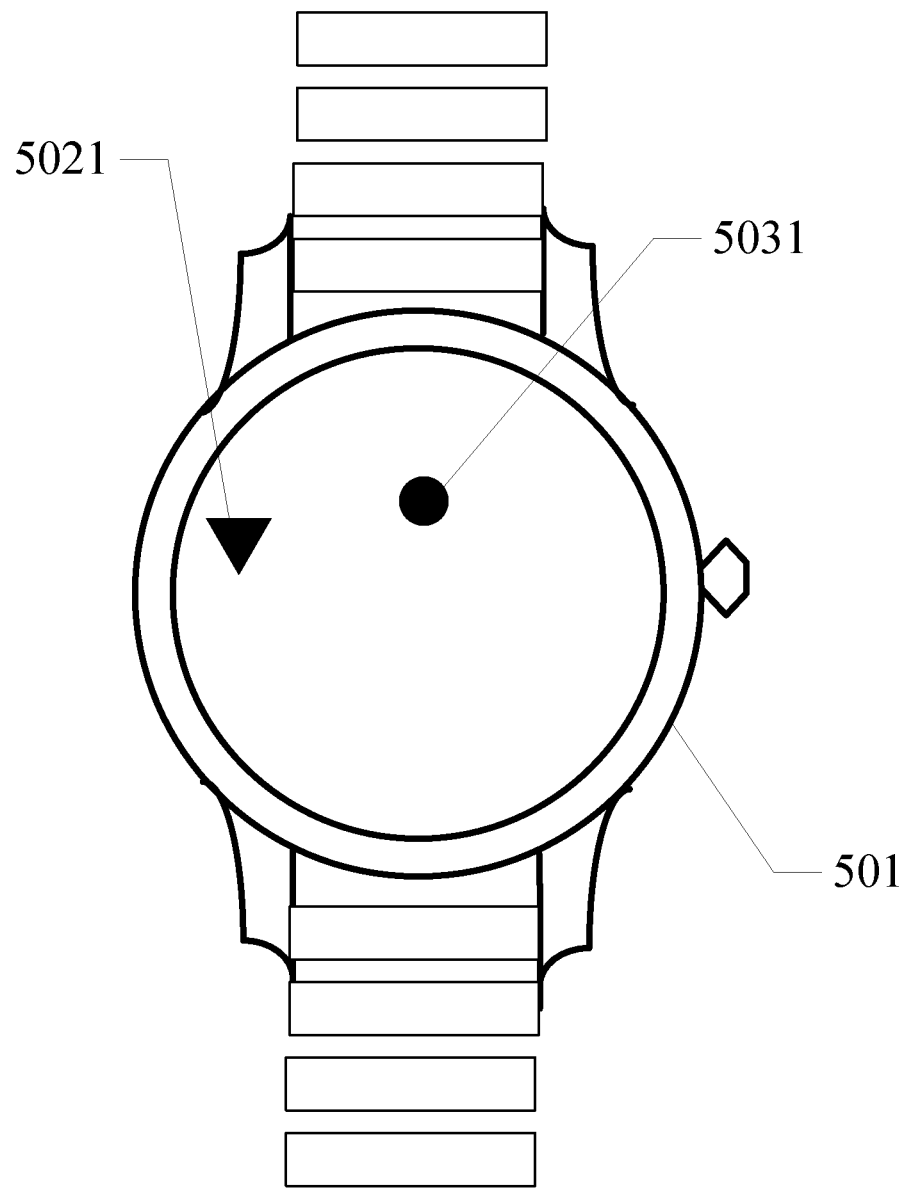
FIG. 5 is a structural diagram of a smart wrist watch in the present invention.

The present invention still discloses a smart wrist watch, FIG. 5 is a structural diagram of a smart wrist watch in the present invention, and as shown in FIG. 5, the smart wrist watch includes a metal watch casing 501, a wireless communication unit provided in the watch casing 501, a human body information detection unit, and a signal selection unit for screening out a signal. The wireless communication unit includes a wireless antenna 5021, all or part of the metal watch casing 501 is used as an antenna area for setting the wireless antenna, and a common conductor is provided for the antenna area. The wireless communication unit, the human body information detection unit, and the common conductor are all provided inside the metal watch casing 501, and hence are not shown in FIG. 5.

The human body information detection unit includes at least two detection contact points, one of the detection contact points 5031 is provided in the antenna area; the detection contact point 5031 in the antenna area and the wireless antenna 5021 are connected with one end of the common conductor 105, respectively, and the other end of the common conductor is connected with the signal selection unit; the signal selection unit screens out a signal from the wireless antenna 5021 out of signals transmitted on the common conductor, sends the signal to the wireless communication unit, screens out a signal from the detection contact point 5031 out of the signals transmitted on the common conductor and sends the signal to the human body information detection unit.

It can be seen that in the above embodiment, by setting the wireless antenna and the detection contact point in the metal watch casing of the smart wrist watch, it is possible to avoid the additional setting of the detection contact point and the compression of the conductor to the internal space of the smart terminal, and it is also possible to reduce the complexity of setting the two conductors on a PCB board circuit inside the smart terminal. In addition, by setting the detection contact point on the metal watch casing, the contact area between the detection contact point and the human body may be increased, thereby improving the accuracy of the detection by the human body information detection unit.

Figure 6:
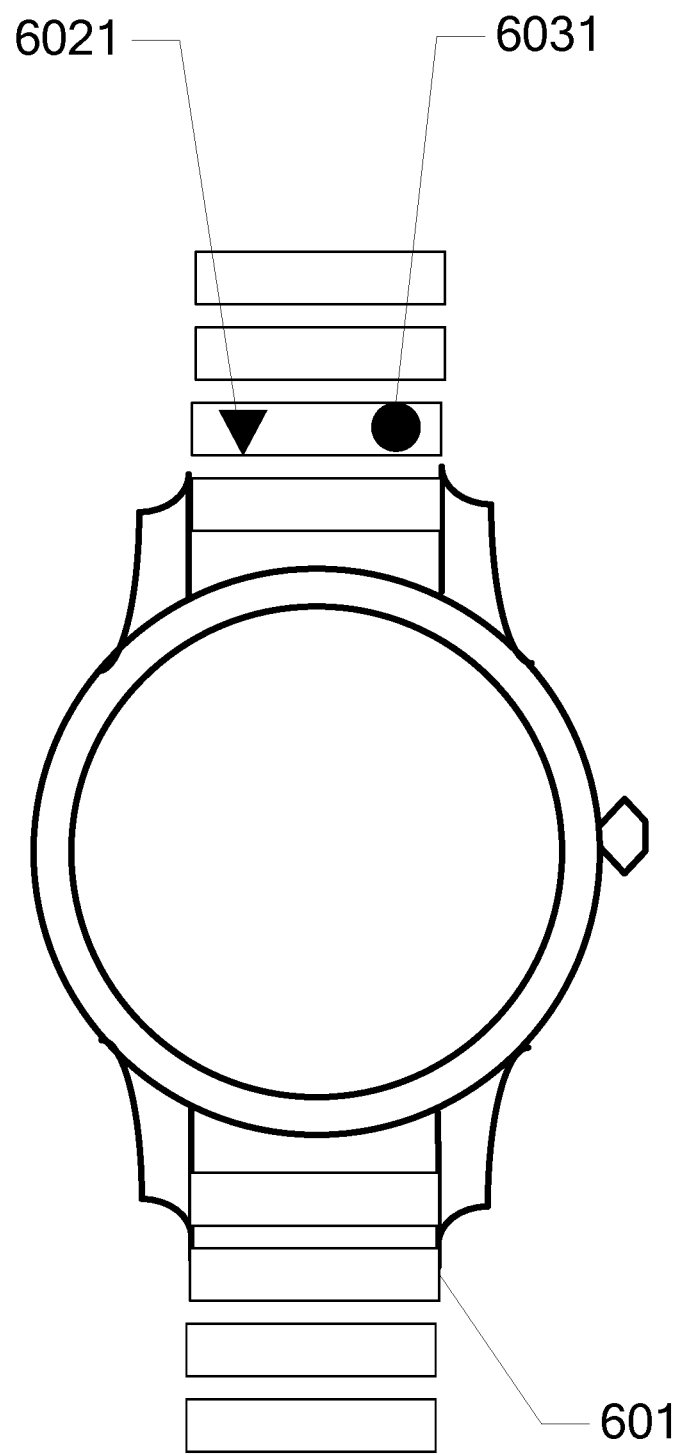
FIG. 6 is a structural diagram of another smart wrist watch in the present invention.

The present invention still discloses a smart wrist watch, FIG. 6 is a structural diagram of another smart wrist watch in the present invention, and as shown in FIG. 6, the smart wrist watch 601 includes a metal watch band, a wireless communication unit of which at least part of a wireless antenna 6021 is provided on the metal watch band 601, a human body information detection unit provided in a watch casing, and a signal selection unit for screening out a signal.

The wireless communication unit includes a wireless antenna 6021, all or part of the metal watch band 601 is used as an antenna area for setting the wireless antenna 6021, and a common conductor is provided for the antenna area. The wireless communication unit, the human body information detection unit, and the common conductor are all provided inside the metal watch band 601, and hence are not shown in FIG. 6.

The human body information detection unit includes at least two detection contact points, and one of the detection contact points 6031 is provided in the antenna area; the detection contact point 6031 in the antenna area and the wireless antenna 6021 are connected with one end of the common conductor, respectively, and the other end of the common conductor is connected with the signal selection unit; the signal selection unit screens out a signal from the wireless antenna 6021 out of a signal transmitted on the common conductor, sends the signal to the wireless communication unit, screens out a signal from the detection contact point 6031 out of the signal transmitted on the common conductor and sends the signal to the human body information detection unit.

It can be seen that in the above embodiment, by setting the wireless antenna and the detection contact point in the metal watch casing of the smart wrist band, it is possible to avoid the additional setting of the detection contact point and the compression of the conductor to the internal space of the smart terminal, and it is also possible to reduce the complexity of setting the two conductors on a PCB board circuit inside the smart terminal. In addition, by setting the detection contact point on the metal watch band, not only the contact area between the detection contact point and the human body may be increased, but also the distance between the two detection contact points of the human body information detection unit may be prolonged, thereby improving the accuracy of detection by the human body information detection unit.

In the embodiment of the smart wrist watch shown in FIG. 5 or FIG. 6 of the present invention, the signal selection unit includes a high frequency switch;

the high frequency switch screens out a signal having a frequency higher than a first preset value out of the signal transmitted on the common conductor, to use the signal as the signal from the wireless antenna, and high frequency switch gets through a branch connected with the wireless communication unit, and shuts down a branch connected with the human body information detection unit, to send the signal which is screened out to the wireless communication unit;

The high frequency switch screens out a signal having a frequency higher than a second preset value out of the signal transmitted on the common conductor, to use the signal as the signal from the detection contact point, and shuts down a branch connected with the wireless communication unit, and the high frequency switch gets through the branch connected with the human body information detection unit, to send the signal which is screened out to the human body information detection unit.

In another embodiment of the smart wrist watch shown in FIG. 5 or FIG. 6 of the present invention, the signal selection unit includes a high-pass filter and a low-pass filter;

the other end of the common conductor is connected with the high-pass filter and the low-pass filter, respectively, the high-pass filter is connected with the wireless communication unit, and the low-pass filter is connected with the human body information detection unit;

the high-pass filter screens out the signal from the wireless antenna out of the signal transmitted on the common conductor and sends the signal to the wireless communication unit, and the low-pass filter screens out the signal from the detection contact point out of the signal transmitted on the common conductor and sends the signal to the human body information detection unit.

In the embodiment of the smart wrist watch shown in FIG. 5 or FIG. 6 of the present invention, human body information data detected by the detection contact point include heart rate data, blood pressure data, pulse data and body temperature data;

the human body information detection unit calculates the human body state detection result based on the human body information data detected by the detection contact point.

In one embodiment of the present invention, the wireless communication unit may be one or more of the followings: a Bluetooth module, a WIFI module, a radio frequency module, a 3G communication module and a 4G communication module.

It needs to be described supplementally that in one embodiment of the present invention, the detected human body information data may be displayed directly on the smart wrist watch shown in FIG. 5 or FIG. 6; it is also possible to provide a wireless communication module within the smart wrist watch, the human body information detection unit is connected with the wireless communication module, by the wireless communication module, and transmits the detected human information data to external devices such as a mobile phone, a tablet computer and so on to be displayed, so that a user may obtain the corresponding human information data conveniently in time.

In summary, in the smart terminal and the smart watch provided by the present invention, all or part of the metal housing is provided as an antenna area, and a detection point of the human body information detection unit is provided in the antenna area. Therefore, the distance between the two contact points of the body information detection unit is longer, and it is also possible to improve the contact area between the detection contact point and the human body, thereby improving the stability of the test result of the human body information detection unit. Furthermore, in the present invention, the detection contact point of the human body information detection unit shares the conductor with the wireless antenna, saving the separately provided detection contact point and the corresponding alignment. Therefore, the overall structure of the smart terminal is more compact, and the human body information data collected by the human body information detection unit are also more accurate. It can be seen that the technical solution of the present invention solves the problem that portable products such as the smart wrist watch in the prior art are small in size and that the internally provided detection contact point is usually smaller in area, which have defects that affect the test results.

The foregoing is merely a preferred embodiment of the present invention and is not intended to limit the protection scope of the present invention. Any modification, equivalent substitution, improvement, and the like made within the spirit and principles of the present invention are intended to be included within the protection scope of the present invention.

The invention claimed is:

1. A smart wrist watch, comprising:
a metal watch band;
a wireless communication unit of which at least part of a wireless antenna is provided on the metal watch band;
a human body information detection unit provided in a watch casing; and
a signal selection unit for screening out a signal;
wherein:
the wireless communication unit comprises the wireless antenna, all or part of the metal watch band is used as an antenna area for setting the wireless antenna, and a common conductor is provided for the antenna area;
the human body information detection unit comprises at least two detection contact points, and one of the detection contact points is provided in the antenna area;
the detection contact point in the antenna area and the wireless antenna are connected with one end of the common conductor, respectively;
the other end of the common conductor is connected with the signal selection unit; and
the signal selection unit screens out a signal from the wireless antenna out of a signal transmitted on the common conductor, sends the signal to the wireless communication unit, screens out a signal from the detection contact point out of the signal transmitted on the common conductor and sends the signal to the human body information detection unit.

2. The smart wrist watch according to claim 1, wherein:
the signal selection unit comprises a high frequency switch;
the high frequency switch screens out a signal having a frequency higher than a first preset value out of the signal transmitted on the common conductor, using the signal as the signal from the wireless antenna, and the high frequency switch gets through a branch connected with the wireless communication unit, and shuts down a branch connected with the human body information detection unit, sending the signal which is screened out to the wireless communication unit; and
the high frequency switch screens out a signal having a frequency lower than a second preset value out of the signal transmitted on the common conductor, using the signal as the signal from the detection contact point, and the high frequency switch shuts down a branch connected with the wireless communication unit, and gets through a branch connected with the human body information detection unit, sending the signal which is screened out to the human body information detection unit.

3. The smart wrist watch according to claim 1, wherein:
the signal selection unit comprises a high-pass filter and a low-pass filter;
the other end of the common conductor is connected with the high-pass filter and the low-pass filter, respectively, the high-pass filter is connected with the wireless communication unit, and the low-pass filter is connected with the human body information detection unit; and
the high-pass filter screens out the signal from the wireless antenna out of the signal transmitted on the common conductor and sends the signal from the wireless antenna to the wireless communication unit, and the low-pass filter screens out the signal from the detection contact point out of the signal transmitted on the common conductor and sends the signal from the detection contact point to the human body information detection unit.

4. The smart wrist watch according to claim 1, wherein:
human body information data detected by the detection contact point comprise one or more of heart rate data, blood pressure data, pulse data and body temperature data; and
the human body information detection unit calculates the human body state detection result based on the human body information data detected by the detection contact point.

5. The smart wrist according to claim 1, wherein the wireless communication unit is one or more of the following:
a Bluetooth module, a WIFI module, a radio frequency module, a 3G communication module and a 4G communication module.

6. The smart wrist according to claim 5, wherein the smart wrist still comprises a wireless communication module; the human body information detection unit is connected with the wireless communication module, and the human body information detection unit transmits, through the wireless communication module, the detected human body information data to an external intelligent device, so that the external intelligent device displays the detected human body information data.

* * * * *